(12) United States Patent
Stoddard et al.

(10) Patent No.: US 9,966,642 B2
(45) Date of Patent: May 8, 2018

(54) INSULATION OF RECHARGEABLE BATTERY PACK

(71) Applicant: COVIDIEN LP, Mansfield, MA (US)

(72) Inventors: Robert B. Stoddard, Steamboat Springs, CO (US); James S. Cunningham, Boulder, CO (US); William J. Dickhans, Longmont, CO (US); Russell D. Hempstead, Lafayette, CO (US); Eric R. Larson, Boulder, CO (US); Duane E. Kerr, Loveland, CO (US); William H. Nau, Jr., Longmont, CO (US); Anthony B. Ross, Boulder, CO (US); John J. Kappus, Denver, CO (US)

(73) Assignee: Covidien LP, Mansfield, MA (US)

( * ) Notice: Subject to any disclaimer, the term of this patent is extended or adjusted under 35 U.S.C. 154(b) by 0 days. days.

(21) Appl. No.: 15/161,677

(22) Filed: May 23, 2016

(65) Prior Publication Data
US 2016/0268653 A1 Sep. 15, 2016

Related U.S. Application Data

(62) Division of application No. 14/006,628, filed as application No. PCT/US2012/031571 on Mar. 30, 2012, now abandoned.
(Continued)

(51) Int. Cl.
*H01M 10/623* (2014.01)
*H01M 2/10* (2006.01)
(Continued)

(52) U.S. Cl.
CPC ............. *H01M 10/623* (2015.04); *A61L 2/07* (2013.01); *A61L 2/24* (2013.01); *A61L 2/26* (2013.01);
(Continued)

(58) Field of Classification Search
CPC .......... H01M 10/623; H01M 10/0525; H01M 2/1094; H01M 10/486; A61L 2/24; A61L 2/07; A61L 2/28; A61L 2/26
See application file for complete search history.

(56) References Cited

U.S. PATENT DOCUMENTS

| 4,239,836 A | 12/1980 | Picciolo |
| 5,051,322 A | 9/1991 | Hasenauer |

(Continued)

FOREIGN PATENT DOCUMENTS

| WO | 97/19475 A1 | 5/1997 |
| WO | 2010/091170 A1 | 8/2010 |

OTHER PUBLICATIONS

International Search Report from corresponding PCT/US12/31571 dated Jul. 20, 2012.
(Continued)

*Primary Examiner* — Regina M Yoo

(57) ABSTRACT

A battery autoclaving system is provided including a battery pack having a housing, a battery cell disposed within the housing, and an isolation region disposed between the housing and the battery cell. The isolation region may be formed at least partially from at least one of a thermal insulating material, a phase change material or any combination thereof. The system may include a temperature sensor adapted to sense at least one of a temperature of the battery cell temperature of the isolation region. The system may include and an autoclave configured to receive a temperature indication from the temperature sensor and to inhibit autoclaving when the temperature indication exceeds a predetermined value.

4 Claims, 2 Drawing Sheets

Related U.S. Application Data

(60) Provisional application No. 61/469,598, filed on Mar. 30, 2011.

(51) Int. Cl.
    *H01M 10/48* (2006.01)
    *H01M 10/0525* (2010.01)
    *A61L 2/26* (2006.01)
    *A61L 2/07* (2006.01)
    *A61L 2/28* (2006.01)
    *A61L 2/24* (2006.01)

(52) U.S. Cl.
    CPC ............ *A61L 2/28* (2013.01); *H01M 2/1094* (2013.01); *H01M 10/0525* (2013.01); *H01M 10/486* (2013.01); *A61L 2202/14* (2013.01); *H01M 2220/30* (2013.01)

(56) References Cited

U.S. PATENT DOCUMENTS

| | | | |
|---|---|---|---|
| 5,449,571 A | 9/1995 | Longardner et al. | |
| 5,543,248 A | 8/1996 | Dougherty et al. | |
| 5,603,656 A | 2/1997 | Baer et al. | |
| 5,626,982 A | 5/1997 | Kawai et al. | |
| 5,717,313 A | 2/1998 | Grabon | |
| 5,795,664 A | 8/1998 | Kelly | |
| 5,880,438 A | 3/1999 | Parrini et al. | |
| 5,985,482 A | 11/1999 | Horton et al. | |
| 6,148,910 A | 11/2000 | Warner | |
| 6,152,597 A * | 11/2000 | Potega ................... | G01K 1/02 324/104 |
| 6,300,005 B1 | 10/2001 | Kump | |
| 6,468,689 B1 | 10/2002 | Hallaj et al. | |
| 6,696,196 B1 | 2/2004 | Eilers | |
| 7,059,769 B1 * | 6/2006 | Potega ................ | B60L 11/1861 338/22 R |
| 7,205,067 B2 | 4/2007 | Godevais et al. | |
| 7,270,910 B2 | 9/2007 | Yahnker et al. | |
| 7,433,794 B1 * | 10/2008 | Berdichevsky ....... | B60L 3/0046 320/150 |
| 8,076,022 B1 | 12/2011 | Tsukamoto | |
| 8,088,508 B2 | 1/2012 | Fujiwara | |
| 8,485,075 B1 * | 7/2013 | Gauthier ............ | B25B 23/1425 81/177.5 |
| 2004/0012370 A1 | 1/2004 | Miller | |
| 2005/0096661 A1 | 5/2005 | Farrow et al. | |
| 2006/0110657 A1 | 5/2006 | Stanton et al. | |
| 2006/0257724 A1 | 11/2006 | Kwon et al. | |
| 2007/0160494 A1 * | 7/2007 | Sands ...................... | A61L 2/07 422/26 |
| 2009/0148767 A1 | 6/2009 | Yamashita et al. | |
| 2009/0169983 A1 * | 7/2009 | Kumar ................ | H01M 10/659 429/120 |
| 2009/0195216 A1 | 8/2009 | Johnson et al. | |
| 2010/0028758 A1 | 2/2010 | Eaves et al. | |
| 2010/0039071 A1 | 2/2010 | Hansford et al. | |
| 2010/0264876 A1 | 10/2010 | Powell et al. | |
| 2010/0264879 A1 | 10/2010 | Lim et al. | |
| 2010/0273041 A1 | 10/2010 | Lawall et al. | |
| 2011/0086265 A1 | 4/2011 | Suzuki | |
| 2011/0195291 A1 | 8/2011 | Yokoyama et al. | |

OTHER PUBLICATIONS

European Search Report from corresponding EP application No. 12763020 dated Jun. 5, 2013.

* cited by examiner

INSULATION OF RECHARGEABLE BATTERY PACK

CROSS-REFERENCE TO RELATED APPLICATION(S)

The present application is a divisional application of U.S. patent application Ser. No. 14/006,628, filed on Sep. 20, 2013, which is a national stage application of International Application No. PCT/US2012/031571, filed on Mar. 30, 2012, which claims the benefit of and priority to U.S. Provisional Patent Application Ser. No. 61/469,598, filed Mar. 30, 2011; the contents of each of these is incorporated by reference herein in its entirety for all purposes.

BACKGROUND

1. Technical Field

The present disclosure relates to medical instruments and to the use thereof. More particularly, the present disclosure is directed to portable surgical devices and sterilization of components thereof.

2. Background

Portable surgical instruments are known in the medical arts. Portable surgical instruments overcome some of the drawbacks that are typically associated with surgical instruments that draw power from electrical outlets. That is, outlet driven surgical instruments utilize power cords that may create tripping and/or entanglement hazards in an operating room environment.

Typically, the portable surgical instrument includes a battery or battery assembly that is configured to removably couple or "latch" to the portable surgical instrument. In an ideal scenario, the battery or battery assembly remains coupled or "latched" to the portable surgical instrument during the entirety of the surgical procedure. However, in certain instances, the battery or battery assembly has to be uncoupled or "unlatched" from the portable surgical instrument during the surgical procedure. For example, the battery or battery assembly may have to be unlatched from the surgical instrument for sterilization (or re-sterilization), charging (or recharging), replacement, and the like.

As may be appreciated, removable batteries or battery assemblies that are configured to quickly and easily couple or latch to a handpiece of the portable surgical instrument may prove advantageous in the surgical environment.

It may be desirable to re-sterilize a rechargeable battery pack using an autoclave. However, this high temperature method is above the temperature limits of currently available rechargeable battery cells.

SUMMARY

Disclosed is an apparatus and method for insulating a rechargeable battery pack to allow it to survive autoclave sterilization.

In at least one aspect of this disclosure, a method for autoclaving a battery pack includes providing the battery pack, wherein the battery pack includes a housing, a battery cell disposed within the housing, and an isolation region disposed between the housing and the battery cell, the isolation region being formed at least partially from at least one of a thermal insulating material, a phase change material, or a combination thereof.

In another aspect of this disclosure, the method may further include inserting the battery pack into the autoclave, sterilizing the battery pack in the autoclave, and removing the battery pack from the autoclave after sterilization.

In yet another aspect of this disclosure, the battery pack may further include a first and a second outer terminal connected a first and second battery terminal of the battery cell through at least one of the housing and the isolation region.

In yet another aspect of this disclosure, the method may further include providing an autoclave configured to accept the battery pack and to sterilize the battery pack.

In yet another aspect of this disclosure, the method may further include monitoring the temperature of at least one of the housing, the battery cell, and the isolation region.

In yet another aspect of this disclosure, the method may further include providing a sterile terminal cap and placing the sterile terminal cap over at least one of the first or second outer terminals.

In yet another aspect of this disclosure, the battery pack further comprises at least one temperature sensor configured to sense a temperature of at least one of the housing, the isolation region, or the battery cell.

In yet another aspect of this disclosure, the method may further include providing an autoclave configured to accept the battery pack and to sterilize the battery pack, wherein the autoclave is configured to read the at least one temperature sensor and provide an indication of temperature.

In yet another aspect of this disclosure, the isolation region further includes at least two layers, wherein each layer is formed from at least one of a phase change material or an insulation material.

In yet another aspect of this disclosure, a battery pack may include a housing, a battery cell disposed within the housing, and an isolation region disposed between the housing and the battery cell, the isolation region being formed at least partially from at least one of a thermal insulating material, a phase change material, or any combination thereof.

In yet another aspect of this disclosure, the battery pack may further include at least one temperature sensor configured to sense the temperature of at least one of the housing, the isolation region, or the battery cell.

In yet another aspect of this disclosure, the isolation region further includes at least two layers, wherein each layer is formed from at least one of a phase change material or an insulation material.

In yet another aspect of this disclosure, the isolation region is formed from two or more materials selected from the group consisting of a phase change material and an insulation material.

In yet another aspect of this disclosure, the battery pack may further include a sterile terminal cap configured to selectively cover at least one of the first and second outer terminals.

In yet another aspect of this disclosure, the sterile terminal cap may be puncturable such that at least one of the first or second outer terminals may be accessed by piercing or removing a portion of the sterile terminal cap.

In yet another aspect of this disclosure, a battery autoclaving system may include a battery pack having a housing, a battery cell disposed within the housing, and an isolation region disposed between the housing and the battery cell, wherein the isolation region is formed at least in part from at least one of a thermal insulating material, a phase change material, or any combination thereof, a temperature sensor adapted to sense at least one of a temperature of the battery cell temperature of the isolation region, and an autoclave configured to receive a temperature indication from the temperature sensor and to inhibit autoclaving when the temperature indication exceeds a predetermined value.

BRIEF DESCRIPTION OF THE DRAWINGS

Embodiments according to the present disclosure are described, by way of example only, with reference to the accompanying drawings, wherein.

DETAILED DESCRIPTION

Figure 1:
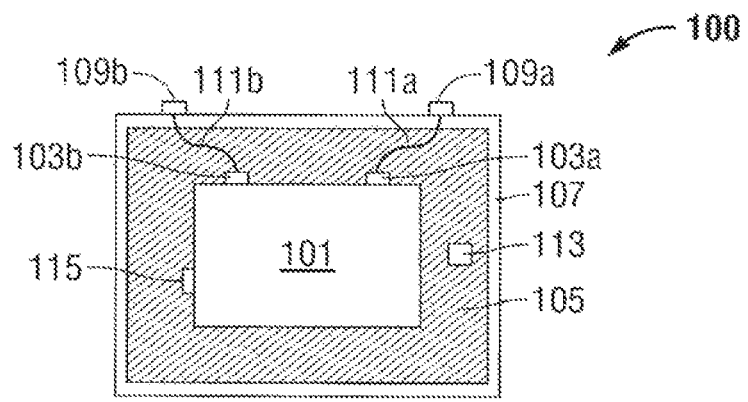
FIG. 1 illustrates an embodiment of a rechargeable battery pack in accordance with the present disclosure.

Particular embodiments of the present disclosure are described hereinbelow with reference to the accompanying drawings; however, the disclosed embodiments are merely examples of the disclosure and may be embodied in various forms. Well-known functions or constructions are not described in detail to avoid obscuring the present disclosure in unnecessary detail. Therefore, specific structural and functional details disclosed herein are not to be interpreted as limiting, but merely as a basis for the claims and as a representative basis for teaching one skilled in the art to variously employ the present disclosure in virtually any appropriately detailed structure.

Like-referenced numerals may refer to similar or identical elements throughout the description of the drawings. As shown in the drawings and described throughout the following description, as is traditional when referring to relative positioning on a surgical instrument, the term "proximal" refers to the end of the apparatus that is closer to the user and the term "distal" refers to the end of the apparatus that is farther away from the user. The term "clinician" refers to any medical professional (e.g., doctor, surgeon, nurse, or the like) who may perform a medical procedure involving the use of embodiments described herein.

In accordance with at least one aspect of the present disclosure, a battery pack for use with a portable surgical instrument is disclosed. Referring to FIG. 1, the battery pack 100 may include an isolation region 105 disposed between at least one battery cell 101 and at least one housing 107, thereby sealing the at least one battery cell 101 and the isolation region 105 inside.

The battery cell 101 may be any suitable battery, including, but not limited to, rechargeable batteries for surgical devices now or in the future known. Non-limiting examples of such a battery cell may include a Li-ion battery, a NiMH battery, a NiCd battery, and the like. The at least one battery cell 101 may include a first terminal 103a and a second terminal 103b.

The housing 107 may be made from at least one of any rigid or semi-rigid material suitable to form a protective layer over the isolation region 105 and/or battery cell 101, including, but not limited to plastic, ceramic, metal, and the like. The housing 107 may further take any desired shaped such that the battery pack 100 may fit into a desired portable surgical device and/or autoclave.

The housing 107 may be selectively sealable and openable such as to allow for removal of the at least one battery cell 101 if desired.

A first outer terminal 109a and a second outer terminal 109b may be disposed on the housing 107, and are configured to conduct electricity. The outer terminals 109a, 109b may form part of the housing 107.

The first outer terminal 109a and a second outer terminal 109b may be connected to the first terminal 103a and second terminal 103b via a first electrical connection 111a and a second electrical connection 111b, respectively.

In some embodiments, the isolation region 105 is formed at least partially from at least one of a thermal insulating material, a phase change material and/or any combination thereof. The isolation region 105 may be formed from an insulating material such as, without limitation, silica aerogel with reinforcing fibers, e.g., Spaceloft™ insulation manufactured by Aspen Aerogel of Northborough, Mass., USA.

In some embodiments, a phase change material is used in addition or alternatively to the insulation material to protect the battery from damaging heat. For example, and without limitation, the phase change material may include sodium sulfate decahydrate (e.g., Glauber's salt) or a similar material whose phase change temperature is below the damage threshold temperature of the battery cell 101.

This isolation region 105 is sized to maintain the temperature of the battery cell (or cells) below its temperature limit when the case is subjected to the known time and temperature profile of an autoclave sterilization cycle.

The battery pack 100 may further include at least one temperature sensor configured to sense the temperature of at least one of the housing 107, the isolation region 105, or the battery cell 101. For example, there may be at least one isolation region temperature sensor 113 and/or at least one battery cell temperature sensor 115.

Figure 2:
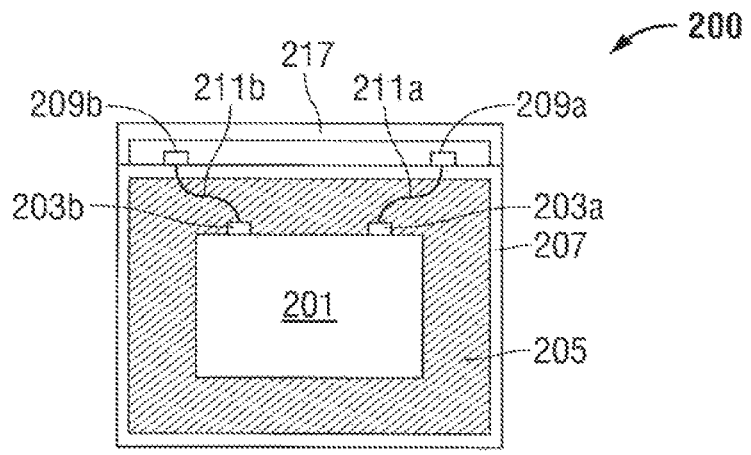
FIG. 2 illustrates another embodiment of a rechargeable battery pack in accordance with the present disclosure.

Referring to FIG. 2, a battery pack 200 may include a battery cell 201, a housing 207, a first outer terminal 209a and a second outer terminal 209b, a first terminal 203a and second terminal 203b, a first electrical connection 211a and a second electrical connection 211b, and an isolation region 205, all similar to the embodiments as described above with respect to FIG. 1.

In some embodiments, and as shown in FIG. 2, battery pack 200 may further include a sterile terminal cap 217 configured to selectively cover at least one of the first outer terminal 209b and second outer terminal 209a. The sterile terminal cap 217 may be puncturable such that access to at least one of the first outer terminal 209b and second outer terminal 209a may be gained by piercing or removing a portion of the sterile terminal cap 217. This allows sterility of the terminals to be maintained underneath the sterile terminal cap 217 after autoclaving and during storage/installation into a surgical device.

Figure 3:
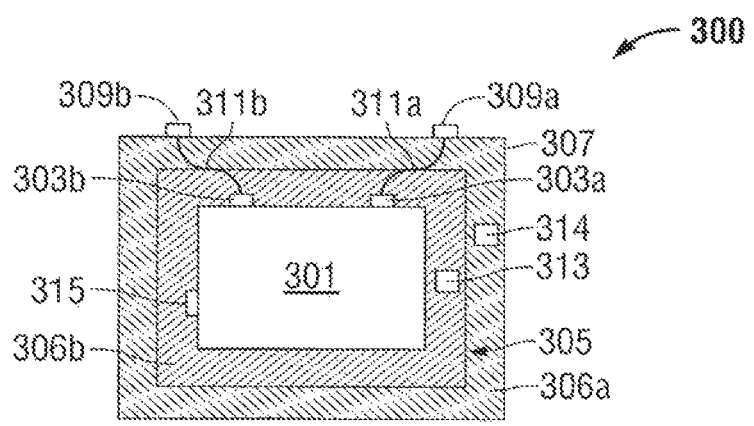
FIG. 3 illustrates yet another embodiment of a rechargeable battery pack in accordance with the present disclosure.

Referring to FIG. 3, a battery pack 300 may include a battery cell 301, a housing 307, a first outer terminal 309a and a second outer terminal 309b, a first terminal 303a and second terminal 303b, a first electrical connection 311a and a second electrical connection 311b, and an isolation region 305, all similar to the embodiments as described above with respect to FIG. 1.

In some embodiments, and as shown in FIG. 3, the isolation region 305 may further include at least two layers, each layer being formed from at least one of a phase change material as described above or an insulation material as described above. In some embodiments where multiple layers include at least one phase change material, the phase change materials of each layer may be selected to have different phase change temperatures. For example, an outer layer 306a may have a lower phase change temperature such that it melts at a first temperature and absorbs heat before an inner layer 306b melts.

The battery pack 300 may further include at least one temperature sensor configured to sense the temperature of at least one of the housing 307, the isolation region 305, or the battery cell 301. For example, there may be at least one isolation region temperature sensor 313 and/or at least one battery cell temperature sensor 315. In embodiments where there are multiple layers in the isolation region 305, there may be additional temperature sensors 314 for any combination of layers as desired.

An embodiment of a battery pack as described herein may protect a battery cell during a heating procedure. For example, during autoclaving, the heat of fusion of the phase change material enables the material to absorb a great deal of thermal energy, thus keeping heat from accumulating in the battery cell and thereby maintaining the cell (or cells) at a safe temperature.

Figure 4:
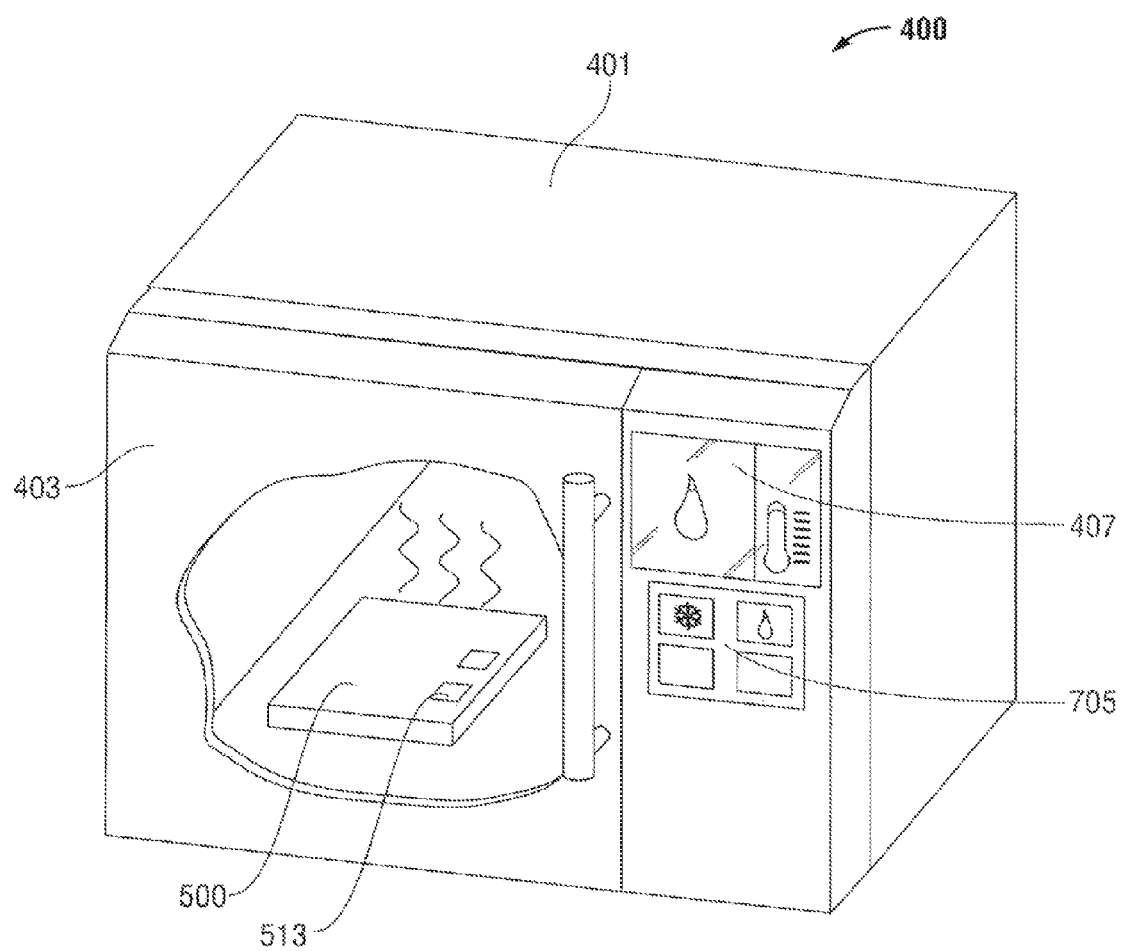
FIG. 4 illustrates an embodiment of a system for autoclaving a battery in accordance with the present disclosure.

Referring to FIG. 4, further disclosed is a battery autoclaving system 400 that may include a battery pack 500 as described herein, a temperature sensor as described above, and an autoclave 401 configured to receive a temperature indication from the temperature sensor and to inhibit autoclaving (e.g., sterilization) when the temperature indication exceeds a predetermined value.

The autoclave may have a controller module designed to periodically or constantly monitor temperature indications from one or more temperature sensors. The controller module 705 may include a processor, memory, and/or interface elements configured to communicate with one or more temperature sensors, an autoclave, and the like. The controller module may further be configured to shut down autoclaving or modify the temperature of autoclaving to avoid battery cell failure. The autoclave may alternatively be manually controlled based on a temperature display wherein the temperature information may be displayed on a text display 407 located on the autoclave 401, the housing, or through any other manner of indication such as audible means or visual display.

In some embodiments, a temperature sensor 513 is operatively associated with the battery pack 500 to enable a user to determine whether it is safe to autoclave the battery pack 500. This may be beneficial in situations such as where heat from a prior, recent autoclaving procedure remains in the phase change material or the battery cell. In one scenario, the phase change material may be fully or partially liquefied (having already undergone a phase change during the previous autoclaving session) and thus not be able to fully absorb the necessary heat from another autoclaving session until it necessarily cools. The temperature information may be displayed on a text display located on the housing or through any other means such as audible means or visual display.

In some embodiments, the temperature sensor 513 may be in operative communication with an autoclave 401 that is configured to receive a temperature signal from the temperature sensor 513 indicative of an internal temperature of the battery pack, e.g., the temperature of the battery cell and/or the phase change material. The autoclave may be further configured to inhibit the autoclaving process in the case that one or more battery cells indicate that an internal temperature thereof exceeds a safe threshold for autoclaving. In an embodiment, the autoclave 401 may automatically determine the condition of any battery placed therein prior to initiating an autoclaving cycle. The autoclave 401 may communicate with the battery by any suitable manner of communication, e.g., by electrical connection (e.g., via mating terminals on the battery and autoclave), by wireless connection (e.g., active or passive RFID tags), and/or or any other suitable communication link between the battery and the autoclave. The autoclave 401 may even have an emergency door release feature to open door 403 and release heat quickly in the event of a near critical temperature reading inside the battery. The autoclave 401 may even have an emergency vent feature to open one or more vents and release heat quickly in the event of a near critical temperature reading inside the battery.

Further disclosed is a method for autoclaving a battery pack. The method may include providing the battery pack as described above.

The method may further include inserting the battery pack into an autoclave, sterilizing the battery pack in the autoclave, and removing the battery pack from the autoclave after sterilizing. The battery pack may be moved from the autoclave to a sterile storage area or into a sterile surgical device to maintain sterility.

The method may further include providing an autoclave configured to accept the battery pack and to sterilize the battery pack.

The method may further include monitoring the temperature of at least one of the housing, the battery cell, and the isolation region. The method may further include modifying the temperature of the autoclave or shutting down the autoclave in response to the monitored temperature.

The method may further include providing a sterile terminal cap and placing the sterile terminal cap over at least one of the first or second outer terminals.

The method may further include providing an autoclave configured to accept the battery pack and to sterilize the battery pack, wherein the autoclave is configure to read the at least one temperature sensor and provide an indication of temperature.

What is claimed is:

1. A battery autoclaving system, comprising:
   an autoclavable battery pack, comprising:
     a housing;
     a battery cell disposed within the housing;
     an isolation region disposed between the housing and the battery cell, the isolation region including two different materials, one of the two different materials being a thermal insulating material and the other of the two different materials being a phase change material;
     a temperature sensor disposed within the isolation region or on the battery cell and adapted to sense at least one of a temperature of the battery cell or a temperature of the isolation region;
     first and second outer terminals; and
     a sterile terminal cap configured to selectively cover at least one of the first or second outer terminals; and
   an autoclave configured to receive a temperature indication from the temperature sensor and to inhibit autoclaving when the temperature indication exceeds a predetermined value.

2. The battery autoclaving system in accordance with claim 1, wherein the isolation region further comprises at least two layers, wherein each layer is formed from at least one of a phase change material or an insulation material.

3. The battery autoclaving system in accordance with claim 1, wherein the battery cell is a Li-ion battery cell.

4. The battery autoclaving system in accordance with claim 1, wherein the sterile terminal cap is puncturable such that at least one of the first or second outer terminals may be accessed by puncturing a portion of the sterile terminal cap.

* * * * *